US006426063B1

(12) United States Patent
Schuler

(10) Patent No.: US 6,426,063 B1
(45) Date of Patent: Jul. 30, 2002

(54) HAIR-TREATMENT COMPOSITIONS COMPRISING OLIGOESTERS

(75) Inventor: Wilfried Schuler, Limburg (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/448,103

(22) Filed: Nov. 23, 1999

(30) Foreign Application Priority Data

Nov. 25, 1998 (DE) .......................................... 198 54 352

(51) Int. Cl.$^7$ ............................ A61K 7/06; A61K 7/075
(52) U.S. Cl. .................... 424/70.11; 424/70.1; 510/119
(58) Field of Search ............................ 424/70.1, 70.11; 510/119

(56) References Cited

U.S. PATENT DOCUMENTS

| 2,826,551 A | 3/1958 | Geen |
| 3,557,039 A | 1/1971 | McIntyre et al. |
| 3,959,280 A | 5/1976 | Furukawa et al. |
| 3,964,500 A | 6/1976 | Drakoff |
| 4,362,837 A | 12/1982 | Teyssie et al. |
| 4,390,522 A | 6/1983 | Jacquet et al. |
| 4,704,272 A | 11/1987 | Oh et al. |
| 4,738,787 A | * 4/1988 | O'Lenick, Jr. et al. |
| 4,741,855 A | 5/1988 | Grote et al. |
| 4,788,006 A | 11/1988 | Bolich, Jr. et al. |
| 4,902,499 A | 2/1990 | Bolish, Jr. et al. |
| 5,211,941 A | 5/1993 | Komori et al. |
| 5,342,611 A | 8/1994 | Komori et al. |
| 6,156,721 A | * 12/2000 | Kwetkat et al. |

FOREIGN PATENT DOCUMENTS

| GB | 849 433 | 9/1960 |

OTHER PUBLICATIONS

Lang, Optimized Soil Release Polymers, Chimica Oggi (Sep. 1998), 16(9), 14–18.*
Derwent Patent Family Report and/or Abstract for German Patent No. 16 17 141 (1973).
Derwent Patent Family Report and/or Abstract for German Patent No. 195 00 841 (1996).
Derwent Patent Family Report and/or Abstract for German Patent No. 22 00 911 (1973).
Derwent Patent Family Report and/or Abstract for European Patent No. 066 944 (1982).
Derwent Patent Family Report and/or Abstract for German Patent No. 444 38 115 (1996).

* cited by examiner

Primary Examiner—Thurman K. Page
Assistant Examiner—Brian K. Seidleck
(74) Attorney, Agent, or Firm—Scott E. Hanf; Susan S. Jackson

(57) ABSTRACT

Hair-treatment compositions which comprise oligoesters prepared by condensation of an aromatic dicarboxylic acid, ethylene glycol and/or propylene glycol and polyethylene glycol and optionally alkylpolyethylene glycol are claimed.

9 Claims, No Drawings

HAIR-TREATMENT COMPOSITIONS COMPRISING OLIGOESTERS

FIELD OF THE INVENTION

The invention relates to hair-treatment compositions, for example hair shampoos, hair conditioners, hair treatments, containing polyesters.

DESCRIPTION OF THE RELATED ART

Frequent bleaching, permanent waving and coloring, but also frequent washing of the hair with degrease surfactants, results in damage to the structure of the hair. The hair becomes brittle and loses its shine. Furthermore, the hair becomes electrostatically charged upon combing, and the roughened surface of the hair causes matting and knotting of the hair. As a result, combing is hindered. Hair-treatment compositions with a combability-improving and conditioning action have thus achieved considerable importance.

Compositions of this type are, for example, frequently distributed in wet hair in the form of a clear haircare conditioner, an aerosol foam or else in emulsion form as so-called cream rinses after the hair has been washed and, depending on the type of hair-treatment composition, either rinsed out with water after a contact time of a few minutes, or else left on the hair.

Active ingredients which are used to improve the structure of the hair are mainly cationic, in particular quaternary ammonium compounds, such as cetyltrimethylammonium chloride, alone or in combination with a variety of waxy additives, such as, for example, hydrocarbons, fatty alcohols and fatty acids. Hair cleansing and hair conditioning in two stages is time-consuming, meaning that many consumers prefer hair compositions with a combined cleansing and conditioning action.

A number of conditioning active ingredients are available for the preparation of conditioning shampoos.

These include oils and oil-like substances such as, for example, liquid hydrocarbon compounds, fatty alcohols, monocarboxylic acid esters, polyalcohol esters, silicones, both soluble, such as, for example, dimethicone copolyols, and insoluble silicones, for example polydimethylsiloxane, and cationic surface-active agents and cationic polymers.

DE-A-195 00 841 discloses hair shampoos based on anionic surfactants and which, in addition to cationic polymers and polysiloxanes, also have alkyloligoglucosides and protein fatty acid condensates. DE-A-44 38 115 proposes hair-treatment compositions comprising alkyl and/or alkenyl oligoglycosides and/or fatty acid N-alkylpolyhydroxyalkylamides and protein abietic acid condensates. Conditioning shampoos which comprise silicones are described in various patents (U.S. Pat. No. 2,826, 551, U.S. Pat. No. 3,964,500, U.S. Pat. No. 4,364,837, GB 849,433, U.S. Pat. No. 4,741,855, U.S. Pat. No. 4,788,006 and U.S. Pat. Nos. 4,902,499, 4,704,272 and in EP 0 461 593). DE 30 48 075 describes the use of quaternary polymers as conditioning agents in hair-treatment compositions.

Hair-treatment compositions comprising the abovementioned constituents often have the disadvantage that their foaming ability is not always satisfactory. This refers on the one hand to the height of the base foam, and also on the other hand to foam stability, in particular in hard water. A further disadvantage is that hair shampoos often leave a rough feel on the hair after they have been rinsed out and impair combability. Cationic agents which are frequently used for haircare impart a sticky feel to damp hair and weigh dry hair down.

Surprisingly, we have found that the incorporation of polyesters into into hair-treatment compositions, significantly improves foaming ability, foam structure and dry combability. In addition, they reduce the rate at which the hair becomes greasy again, and have an antistatic and feel-improving action, and feel pleasant on the skin. They make dry hair loose, shiny and easy to untangle.

Polyesters, under the name of Soil Release Polymers (SRP), have been used for some time in detergent and surface-active cleansers and in fiber preparation because of their soil-release action and for improving the antistatic and slip properties of textile fibers.

The German laid-open specifications DE-A-16 17 141 and DE-A-22 00 911 describe the incorporation of polyterephthalate/polyoxyethylene glycol copolymers or a mixed polymer of polyethylene glycol and polyethylene terephthalate in detergents for improving wash-off of oily/greasy soilings from cotton/polyester blends. U.S. Pat. No. 3,557,039 describes the synthesis of a polyester starting from dimethyl terephthalate and ethylene glycol in the presence of a catalyst; in the synthesis given in U.S. Pat. No. 3,959,280, polyethylene oxide is additionally used as reactant. EP-A-066 944 relates to textile-treatment compositions which comprise a copolyester of ethylene glycol, propylene glycol, aromatic dicarboxylic acid and sulfonated aromatic dicarboxylic acid in specific molar ratios.

SUMMARY OF THE INVENTION

The invention provides hair-treatment compositions comprising oligoesters of the formula

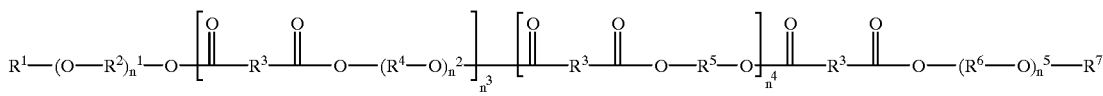

in which $R^1$ and $R^7$ are hydrogen or linear or branched $C_1$- to $C_{18}$-alkyl, $R^2$ and $R^6$ are ethylene, $R^3$ is o-, m- or p-phenylene, $R^4$ is ethylene, $R^5$ is ethylene, 1,2-propylene or random mixtures of any composition of the two, $n^1$ and $n^5$ independently of one another are a number between 1 and 500, $n^2$ is a number from 10 to 140, $n^3$ is a number from 0 to 12, $n^4$ is a number from 7 to 40.

Preferably, independely of one another, $R^1$ and $R^7$ are hydrogen or linear or branched $C_1$- to $C_4$-alkyl, $R^3$ is p-phenylene, $n^1$ and $n^5$ are a number from 3 to 45, $n^2$ is a number from 18 to 70, $n^3$ is a number from 0 to 5, $n^4$ is a number from 8 to 12, $n^3+n^4$ is a number from 12 to 18 or from 25 to 35.

DESCRIPTION OF THE PREFERRED EMBODIMENTS

The oligoesters according to the invention are synthesized from the dicarboxylic acid HOOC—$R^3$—COOH or its dimethyl ester, preferably dimethyl terephthalate, ethylene glycol and/or propylene glycol, polyethylene glycol and optionally $C_1$- to $C_{18}$-alkylpolyethylene glycol by carrying out a transesterification with addition of a catalyst by heating to temperatures of from 160 to about 220° C. firstly at atmospheric pressure and while distilling off the methanol, and then effecting condensation under reduced pressure at temperatures of from 160 to about 240° C. while distilling off excess glycols. Transesterification and condensation catalysts from the prior art are suitable, such as, for example, titanium tetraisopropoxide, dibutyltin oxide or antimony trioxide/calcium acetate.

These oligoesters can be incorporated into any type of hair-treatment composition, for example into shampoos, cream rinses, hair conditioners, hair lotions, waving compositions or aerosol foams. The content of oligoesters in these haircare compositions can vary within wide limits and is generally from 0.1 to 5% by weight, preferably from 0.5 to 3% by weight, in particular from 1 to 2% by weight, based on the hair-treatment composition.

Moreover, the hair-treatment compositions according to the invention comprise the constituents customary in this connection, essentially anionic, nonionic, cationic, zwitterionic or amphoteric surfactants, and auxiliaries and additives such as emulsifiers, refatting agents, biogenic active ingredients, film formers, preservatives, pearlizing agents, dyes.

Anionic surfactants are, in particular, the following compound d their mixtures: alkali metal salts, ammonium salts, amine salts and salts of aminoalcohols of the following compounds: alkyl sulfates, alkyl ether sulfates, alkylamide sulfates and ether sulfates, alkylaryl polyether sulfates, monoglyceride sulfates, alkylsulfonates, alkylamidosulfonates, alkylarylsulfonates, α-olefinsulfonates, alkyl sulfosuccinates, alkyl ether sulfosuccinates, alkylamidosulfosuccinamates, alkyl sulfoacetates, alkylpolyglycerol carboxylates, alkyl phosphates, alkyl ether phosphates, alkyl sarcosinates, alkyl polypeptidates, alkylamidopolypeptidates, alkyl isethionates, alkyl taurates.

Salts of saturated and unsaturated fatty acids, such as oleic acid, ricinoleic acid, palmitic acid, stearic acid, copra oil acid salts or hydrogenated copra oil acid salts, and alkylpolyethoxycarboxylates.

Cationic surfactants are, in particular, quaternary ammonium compounds having a long chain, alkylpyridinium salts, fatty amines of polyethers, imidazoline derivatives.

Nonionic surfactants are, in particular, polyethoxylated, polypropoxylated or polyglycerolated ethers of fatty alcohols, polyethoxylated, polypropoxylated and polyglycerolated fatty acid esters, polyethoxylated esters of fatty acids and of sorbitol, polyethoxylated or polyglycerolated fatty amides.

Amphoteric surfactants are, in particular, alkylaminomono- and dipropionates, betaines, such as N-alkylbetaines, N-alkylsulfobetaines, N-alkylamidobetaines, cycloimidinium compounds, such as alkylimidazolines, asparagine derivatives, where the alkyl group in these surface-active agents preferably has from 1 to 22 carbon atoms.

The hair-treatment compositions according to the invention can comprise, as auxiliaries and additives, emulsifiers such as approximately nonionic emulsifiers, for example ethoxylated or polyglycerolated fatty alcohols, e.g. oleyl alcohol, polyethoxylated with from 10 to 30 mol of ethylene oxide, stearyl alcohol with from 10 to 15 or 20 mol of ethylene oxide, oleyl alcohol, polyglycerolated with 4 mol of glycerol, synthetic fatty alcohols having from 9 to 15 carbon atoms, polyethoxylated with from 5 to 10 mol thylene oxide, sorbitan esters, monoglycerides, polysorbates, polyethylene glycol mono/di-fatty acid esters, highly ethoxylated fatty acid esters, and high molecular weight silicone compounds, such as, for example, dimethylpolysiloxane and phosphoric esters in an amount of from 1 to 25% by weight, or ionic emulsifiers, such as optionally ethoxylated alkyl sulfates, e.g. sodium lauryl sulfate, ammonium lauryl sulfate, ammonium lauryl sulfate, sodium cetyl stearyl sulfate, triethanolamine stearyl sulfate, monoethanolamine lauryl sulfate, sodium lauryl ether sulfate, and monoethanolamine lauryl ether sulfate, these latter emulsifiers being present in concentrations between 0.5 and 15% by weight. Refatting agents which can be used are substances such as, for example, polyethoxylated lanolin derivatives, lecithin derivatives and fatty acid alkanolamides, the latter also serving as foam stabilizers. Preferred thickeners are hydrogenated castor oil, salts of long-chain fatty acids, preferably in amounts up to 5% by weight and in particular in amounts of from 0.5 to 2% by weight, for example sodium, potassium, aluminum, magnesium and titanium stearates or the sodium and/or potassium salts of behenic acid, and also polysaccharides, in particular xanthan gum, guar guar, agar agar, alginates and tyloses, carboxymethylcellulose and hydroxyethylcellulose, and also relatively high molecular weight polyethylene glycol mono- and diesters of fatty acids, polyacrylates, polyvinyl alcohol and polyvinylpyrrolidone, and electrolytes such as sodium chloride and ammonium chloride.

Biogenic active ingredients are, for example, taken to mean plant extracts, protein hydrolyzates and vitamin complexes. Customary film formers are, for example, chitosan, microcrystalline chitosan, quaternized chitosan, polyvinylpyrrolidone, vinylpyrrolidone/vinyl acetate copolymers, polymers of the acrylic acid series, quaternary cellulose derivatives and similar compounds. Suitable preservatives are, for example, phenoxyethanol, formaldehyde solution, parabens, pentadiol or sorbic acid. Suitable pearlizing agents are, for example, glycol distearic esters such as ethylene glycol distearate, but also fatty acid monoglycol esters or triethylene glycol distearate. Dyes which can be used are the substances which are suitable and approved for cosmetic purposes, such as are listed, for example, in the publication "Kosmetische Farbemittel" [Cosmetic Colorants] from the Farbkommission der Deutschen Forschungsgemeinschaft, published in Verlag Chemie, Weinheim, 1984, p. 81–106. These dyes are usually used in concentrations of from 0.001 to 0.1% by weight, based on the overall mixture. The desired viscosity can be adjusted by adding water and/or organic solvents or by adding a combination of organic solvents and thickeners.

By adding, according to the invention, the oligoesters to hair-treatment compositions, in particular to hair shampoos, hair conditioners and hair treatments, damage to the hair can be eliminated, regreasing of the hair can be delayed and the hair finish and hair shine can be improved.

The examples below serve to illustrate the invention in more detail without limiting it thereto.

EXAMPLES

| | Hair shampoo I | |
|---|---|---|
| A | Genapol LRO, liquid | 35.00% |
| B | Genapol AMG | 8.00% |
| | SRC-Polymer | 1.00% |
| | perfume oil | 0.30% |
| | Gelita Sol C | 1.00% |
| | water | 42.20% |
| | dye solution | q.s |
| | preservative | q.s. |
| | Genagen CAB | 12.00% |
| | Genapol L-3 | 1.00% |
| C | sodium chloride | |

Preparation:
Stir the components B into A one after the other.
If necessary, regulate the pH.
Finally, adjust the viscosity using C.

| | Hair shampoo II | |
|---|---|---|
| A | Genapol LRO, liquid | 40.00% |
| | SRC-Polymer | 1.50% |
| B | perfume oil | 0.30 |
| C | water | 51.00% |
| D | sodium hydroxide | 0.20% |
| E | Hostapon LEC | 4.20% |
| | Genapol L-3 | 2.00% |
| | dye solution | q.s |
| | preservative | q.s. |
| F | sodium chloride | 1.00% |

Preparation:
Mix B with A.
Dissolve D in C, then stir into 1.
Stir the components of E into 1 one after the other.
If necessary, regulate the pH.
Finally, adjust the viscosity using F.

| | Hair shampoo III | |
|---|---|---|
| A | Genapol LRO, liquid | 35.00% |
| | SRC-Polymer | 1.45% |
| B | Hostapon LEC | 5.30% |
| | sodium hydroxide solution (50% strength) | 0.70% |
| | perfume oil | 0.30% |
| | Genapol L-3 | 1.00% |
| | water | 47.00% |
| | D-Panthenol | 0.50% |
| | Genagen CAB | 8.00% |
| | Dye solution | q.s. |
| | Preservative | q.s. |
| C | Sodium chloride | |

Preparation:
Stir the components of A into B one after the other.
If necessary, regulate the pH.
Finally, adjust the viscosity using C.

| | Hair shampoo IV | |
|---|---|---|
| A | Genapol LRO, liquid | 30.00% |
| | SRC-Polymer | 1.00% |

-continued

| | Hair shampoo IV | |
|---|---|---|
| B | Genapol SBE | 6.00% |
| | perfume oil | 0.30% |
| | water | 54.00% |
| | Genapol L-3 | 2.00% |
| | Genagen CAB | 5.00% |
| | dye solution | q.s. |
| | preservative | q.s. |
| C | sodium chloride | 1.70% |

Preparation:
Stir the components of B into A one after the other.
If necessary, regulate the pH.
Finally, adjust the viscosity using C.

| | Hair shampoo V | |
|---|---|---|
| A | Genapol LRO, liquid | 30.00% |
| | SRC-Polymer | 1.00% |
| B | Genapol AMG | 8.00% |
| | Hostapon KCG | 5.00% |
| | perfume oil | 0.30% |
| | water | 45.70% |
| | dye solution | q.s. |
| | preservative | q.s. |
| | Genagen CAB | 6.00% |
| | Genapol L-3 | 2.00% |
| C | sodium chloride | 2.00% |

Preparation:
Stir the components of B into A one after the other.
If necessary, regulate the pH.
Finally, adjust the viscosity using C.

Chemical names of the commercial products used

| ®Genapol LRO | lauryl alcohol ether sulfate (Clariant GmbH) |
|---|---|
| ®Genapol AMG | magnesium amide ether sulfate (Hoechst AG) |
| ®Gelita Sol | Chydrolyzed collagen (Dt. Gelatine Fab.) |
| ®Genagen CAB | cocamidopropylbetaine (Hoechst AG) |
| ®Genapol L-3 | lauryl alcohol with 3 mol of ethylene oxide (Hoechst AG) |
| ®Hostapon LEC | lauroyl ether carboxylic acid (Hoechst AG) |
| ®Genapol SBE | lauryl sulfosuccinate |
| ®Hostapon KCG | sodium cocoyl glutamate (Hoechst AG) |
| SRC-Polymer: | nonionic polyester (soil release polyester) |

What is claimed is:
1. A method for reducing the regreasing rate of hair, the method comprising treating hair with an effective amount of a hair-treatment composition, wherein the hair-treatment composition comprises oligoesters of the formula 1

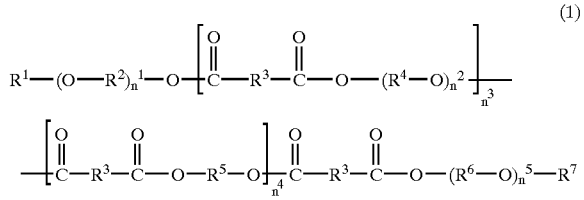

in which
$R^1$ and $R^7$ are hydrogen or linear or branched $C_1$- to $C_{18}$-alkyl, $R^2$ and $R^6$ are ethylene, $R^3$ is o-, m-, or p-phenylene, $R^4$ is ethylene, $R^5$ is ethylene, 1,2-propylene or random mixtures of any composition of the two, $n^1$ and $n^5$ independently of one another are a number between 1 and 500, $n^2$ is a number from 10 to 140, $n^3$ is a number from 0 to 12, $n^4$ is a number from 7 to 40.

2. The method according to claim 1, wherein the hair-treatment composition comprises the oligoester of the formula 1 in which $R^1$ and $R^7$ are hydrogen or linear or branched $C_1$–$C_4$-alkyl, $R^3$ is p-phenylene, $n^1$ and $n^5$ are a number from 3 to 45, $n^2$ is a number from 18 to 70, $n^3$ is a number from 0 to 5, $n^4$ is a number from 8 to 12, $n^3+n^4$ is a number from 12 to 18 or from 25 to 35.

3. The method according to claim 1, wherein the hair-treatment composition comprises from 0.1 to 5% by weight of the oligoester, based on the hair-treatment composition.

4. A method for improving the dry combability of hair comprising treating hair with an effective amount of a hair-treatment composition, wherein the hair-treatment composition comprises oligoesters of the formula 1

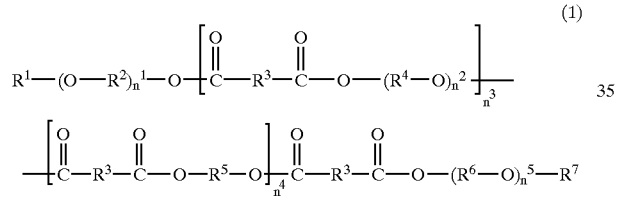

in which $R^1$ and $R^7$ are hydrogen or linear or branched $C_1$- to $C_{18}$-alkyl, $R^2$ and $R^6$ are ethylene, $R^3$ is o-, m-, or p-phenylene, $R^4$ is ethylene, $R^5$ is ethylene, 1,2-propylene or random mixtures of any composition of the two, $n^1$ and $n^5$ independently of one another are a number between 1 and 500, $n^2$ is a number from 10 to 140, $n^3$ is a number from 0 to 12, $n^4$ is a number from 7 to 40.

5. The method according to claim 4, wherein the hair-treatment composition comprises the oligoester of the formula 1 in which $R^1$ and $R^7$ are hydrogen or linear or branched $C_1$–$C_4$-alkyl, $R^3$ is p-phenylene, $n^1$ and $n^5$ are a number from 3 to 45, $n^2$ is a number from 18 to 70, $n^3$ is a number from 0 to 5, $n^4$ is a number from 8 to 12, $n^3+n^4$ is a number from 12 to 18 or from 25 to 35.

6. The method according to claim 4, wherein the hair-treatment composition comprises from 0.1 to 5% by weight of the oligoester, based on the hair-treatment composition.

7. A method for making dry hair loose, shiny and easy to entangle, the method comprising treating hair with an effective amount of a hair-treatment composition, wherein the hair-treatment composition comprises oligoesters of the formula 1

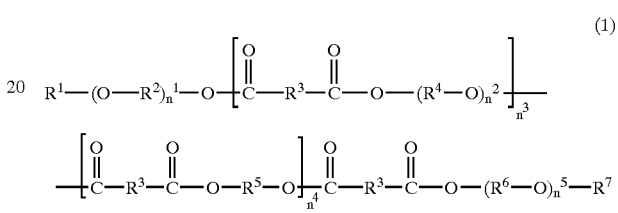

in which $R^1$ and $R^7$ are hydrogen or linear or branched $C_1$- to $C_{18}$-alkyl, $R^2$ and $R^6$ are ethylene, $R^3$ is o-, m-, or p-phenylene, $R^4$ is ethylene, $R^5$ is ethylene, 1,2-propylene or random mixtures of any composition of the two, $n^1$ and $n^5$ independently of one another are a number between 1 and 500, $n^2$ is a number from 10 to 140, $n^3$ is a number from 0 to 12, $n^4$ is a number from 7 to 40.

8. The method according to claim 7, wherein the hair-treatment composition comprises the oligoester of the formula 1 in which $R^1$ and $R^7$ are hydrogen or linear or branched $C_1$–$C_4$-alkyl, $R^3$ is p-phenylene, $n^1$ and $n^5$ are a number from 3 to 45, $n^2$ is a number from 18 to 70, $n^3$ is a number from 0 to 5, $n^4$ is a number from 8 to 12, $n^3+n^4$ is a number from 12 to 18 or from 25 to 35.

9. The method according to claim 7, wherein the hair-treatment composition comprises from 0.1 to 5% by weight of the oligoester, based on the hair-treatment composition.

* * * * *